(12) United States Patent
Turos et al.

(10) Patent No.: US 8,093,027 B2
(45) Date of Patent: Jan. 10, 2012

(54) METHOD FOR PRODUCING BIOCOMPOSITE COMPRISING COLLAGEN AND POLYMER

(75) Inventors: Edward Turos, Wesley Chapel, FL (US); Thomas J. Koob, Tampa, FL (US); Kerriann Robyn Greenhalgh, Tampa, FL (US)

(73) Assignee: University of South Florida, Tampa, FL (US)

( * ) Notice: Subject to any disclaimer, the term of this patent is extended or adjusted under 35 U.S.C. 154(b) by 1094 days.

(21) Appl. No.: 11/901,209

(22) Filed: Sep. 13, 2007

(65) Prior Publication Data
US 2008/0124371 A1 May 29, 2008

Related U.S. Application Data

(60) Provisional application No. 60/844,290, filed on Sep. 13, 2006.

(51) Int. Cl.
*C12N 11/02* (2006.01)
*C12N 11/08* (2006.01)
*C12N 11/04* (2006.01)
(52) U.S. Cl. .......................... 435/177; 435/180; 435/182
(58) Field of Classification Search .................... None
See application file for complete search history.

(56) References Cited

U.S. PATENT DOCUMENTS

| | | | |
|---|---|---|---|
| 3,920,592 A * | 11/1975 | Dykstra et al. | 524/498 |
| 4,693,715 A | 9/1987 | Abel, Jr. | |
| 5,108,428 A | 4/1992 | Capecchi et al. | |
| 5,114,627 A | 5/1992 | Civerchia | |
| 5,162,430 A * | 11/1992 | Rhee et al. | 525/54.1 |
| 5,304,595 A | 4/1994 | Rhee et al. | |
| 5,308,889 A | 5/1994 | Rhee et al. | |
| 5,420,248 A | 5/1995 | Devictor et al. | |
| 5,507,804 A | 4/1996 | Llanos | |
| 5,523,348 A | 6/1996 | Rhee et al. | |
| 5,836,313 A | 11/1998 | Perez et al. | |
| 5,863,984 A * | 1/1999 | Doillon et al. | 525/54.1 |
| 6,106,552 A | 8/2000 | Lacombe et al. | |
| 6,277,394 B1 | 8/2001 | Sierra | |
| 6,565,960 B2 | 5/2003 | Koob et al. | |
| 6,713,537 B1 | 3/2004 | Ueda et al. | |
| 6,821,530 B2 | 11/2004 | Koob et al. | |
| 6,887,933 B2 | 5/2005 | Even | |
| 6,974,679 B2 | 12/2005 | Andre et al. | |
| 6,976,997 B2 | 12/2005 | Noolandi et al. | |
| 7,162,289 B2 | 1/2007 | Shah et al. | |
| 2005/0020506 A1 | 1/2005 | Drapeau et al. | |
| 2006/0008500 A1 | 1/2006 | Chavan et al. | |
| 2006/0100138 A1 | 5/2006 | Olsen et al. | |
| 2006/0129234 A1 | 6/2006 | Phaneuf et al. | |
| 2007/0190160 A1 | 8/2007 | Turos et al. | |

FOREIGN PATENT DOCUMENTS

| | | |
|---|---|---|
| EP | 0177573 B1 | 1/1992 |
| WO | WO 2004/101017 A2 | 11/2004 |
| WO | WO 2005/020933 | 3/2005 |

OTHER PUBLICATIONS

Koob, T. et al. "Material Properties of Polymerized NDGA-collagen composite fibers: development of biologically based tendon constructs" *Biomaterials*, 2002, pp. 203-212, vol. 23.
Koob, T. et al. "Mechanical and thermal properties of novel polymerized NDGA-gelatin hydrogels" *Biomaterials*, 2003, pp. 1285-1292, vol. 24.
Koob, T. et al. "Biocompatibility of NDGA-polymerized collagen fibers. I. Evaluation of cytotoxicity with tendon fibroblasts in vitro" *J Biomed Mater Res*, 2001, pp. 31-39, vol. 56, No. 1.
Koob, T. at al. "Biocompatibility of NDGA-polymerized collagen fibers. II. Attachment, proliferation, and migration of tendon fibroblasts in vitro" *J Biomed Mater Res*, 2001, pp. 40-48, vol. 56, No. 1.
Koob, T. J. "Biomimetic approaches to tendon repair" *Comp Biochem Physiol A Mol Integr Physiol*, 2002, pp. 1171-1192, vol. 133, No. 4.
Koob, T.J. "Collagen Fixation" *Encyclopedia of biomaterials and biomedical engineering*, Wnek, G.E., Bowlin, GL., editors. 2004, pp. 335-347, New York: Marcel Dekker.
Ahmed, S. et al. "Tissue Implanted Glucose Needle Electrodes: Early Sensor Stabilisation and Achievement of Tissue-Blood Correlation During the Run in Period" *Analytica Chimica Acta*, 2005, pp. 153-161, vol. 537.
Norton, L.W. et al. "In vitro characterization of vascular endothelial growth factor and dexamethasone releasing hydrogels for implantable probe coatings" *Biomaterials*, 2005, pp. 3285-3297, vol. 26.
Quinn, C.A.P. et al. "Biocompatible, Glucose-Permeable Hydrogel for in Situ Coating of Implantable Biosensors" *Biomaterials*, 1997, pp. 1665-1670, vol. 18.
Yu, B. et al. "A Long-Term Flexible Minimally-Invasive Implantable Glucose Biosensor Based on an Epoxy-Enhanced Polyurethane Membrane" *Biosensors and Bioelectronics*, 2006, pp. 2275-2282, vol. 21.
Zong, S. at al. "Hydrogen Peroxide Biosensor Based on Hemoglobin Modified Zirconia Nanoparticles-Grafted Collagen Matrix" *Analytica Chimica Acta*, 2007, pp. 361-366, vol. 582.
Angele, P. et al. "Influence of different collagen species on physicochemical properties of crosslinked collagen matrices" *Biomaterials*, 2004, pp. 2831-2841, vol. 25.
Armour, J.C. et al. "Application of chronic intravascular blood glucose sensor in dogs" *Diabetes*, 1990, pp. 1519-1526, vol. 39, No. 12, abstract.
Ash, S.R. et al. "Subcutaneous capillary filtrate collector for measurement of blood glucose" *Asaio J*, 1992, pp. M416-20, vol. 38, No. 3, abstract.
Barbani, N. et al. "Bioartificial materials based on collagen: 1. Collagen cross-linking with gaseous glutaraldehyde" *J Biomater Sci Polym Ed*, 1995, pp. 461-469, vol. 7, No. 6, abstract.
Bindra, D.S. et at "Design and in vitro studies of a needle-type glucose sensor for subcutaneous monitoring" *Anal Chem*, 1991, pp. 1692-1696, vol. 63, abstract.

(Continued)

*Primary Examiner* — David Naff
(74) *Attorney, Agent, or Firm* — Saliwanchik, Lloyd & Eisenschenk (57) ABSTRACT

The present invention concerns a biocomposite useful in artificial tissue replacement, methods for its production, and methods of use. The biocomposite can be implanted into humans or animals as an artificial tissue for treatment of a tissue defect. The biocomposite can be formed or manipulated into a desired shape for implantation.

11 Claims, 6 Drawing Sheets

OTHER PUBLICATIONS

Ertefai, S. et al. "Physiological preparation for studying the response of subcutaneously implanted glucose and oxygen sensors" *J Biomed Eng*, Sep. 1989, pp. 362-368, vol. 11, No. 5, abstract.

Frost, M.C. et al. "Implantable chemical sensors for real-time clinical monitoring: progress and challenges" *Current Opinion in Chemical Biology*, 2002, pp. 633-641, vol. 6.

Huang-Lee, L.L.H. et al. "Biochemical changes and cytotoxicity associated with the degradation of polymeric glutaraldehyde derived crosslinks" *Journal of Biomedical Materials Research*, 1990, pp. 1185-1201, vol. 24.

Johnson, K.W. et al. "In vivo evaluation of an electroenzymatic glucose sensor implanted in subcutaneous tissue" *Biosensors & Bioelectronics*, 1992, pp. 709-714, vol. 7.

Joseph et al. "Glucose Sensors" *Encyclopedia of biomaterials and biomedical engineering*, Wnek G.E., Bowlin G.L., editors., 2004, pp. 683-692, New York: Marcel Dekker, abstract.

Kerner, W. et al. "The function of a hydrogen peroxide-detecting electroenzymatic glucose electrode is markedly impaired in human sub-cutaneous tissue and plasma" *Biosensors & Bioelectronics*, 1993, pp. 473-482, vol. 8.

Khor, E. "Methods for the treatment of collagenous tissues for bioprostheses" *Biomaterials*, 1997, pp. 95-105, vol. 18, No. 2.

Koudelka, M. et al. "In-vivo behaviour of hypodermically implanted microfabricated glucose sensors" *Biosensors & Bioelectronics*, 1991, pp. 31-36, vol. 6.

Lee, C.H. et al. "Biomedical applications of collagen" *International Journal of Pharmaceutics*, 2001, pp. 1-22, vol. 221.

Lee, S. et al. "Glucose measurements with sensors and ultrasound" *Ultrasound in Med. & Biol.*, 2005, pp. 971-977, vol. 31, No. 7.

Long, N. et al. "Strategies for testing long-term transcutaneous amperometric glucose sensors" *Diabetes Technology & Therapeutics*, 2005, pp. 927-936, vol. 7, No. 6.

Meyerhoff, C. et al. "On line continuous monitoring of subcutaneous tissue glucose in men by combining portable glucosensor with microdialysis" *Diabetologia*, 1992, pp. 1087-1092, vol. 35.

Moscone, D. et al. "Microdialysis and glucose biosensor for in vivo monitoring" *Ann Biol Clin (Paris)*, 1992, pp. 323-327, vol. 50, No. 5, abstract.

Moussy, F. et al. "Performance of subcutaneously implanted needle-type glucose sensors employing a novel trilayer coating" *Anal Chem*, 1993, pp. 2072-2077, vol. 65, No. 15.

Moussy, F. et al. "A miniaturized Nafion-based glucose sensor: in vitro and in vivo evaluation in dogs" *Int J Artif Organs*, Feb. 1994, pp. 88-94, vol. 17, No. 2, abstract.

Moussy, F. et al. "Prevention of the rapid degradation of subcutaneously implanted Ag/AgCL reference electrodes using polymer coatings" *Anal Chem*, 1994, pp. 674-679, vol. 66, No. 5.

Moussy, F. et al. "In vitro and in vivo performance and lifetime of perfluorinated ionomer-coated glucose sensors after high-temperature curing" *Anal Chem*, 1994, pp. 3882-3888, vol. 66, No. 22.

Pachence, J.M. "Collagen-based devices for soft tissue repair" *Journal of Biomedical Materials Research (Applied Biomaterials)*, 1996, pp. 35-40, vol. 33.

Patel, V.R. et al, "Preparation and characterization of freeze-dried chitosan-poly(ethylene oxide) hydrogels for site-specific antibiotic delivery in the stomach" *Pharm Res*, 1996, pp. 588-593, vol. 13, No. 4, abstract.

Pickup, J.C. et al. "In vivo molecular sensing in diabetes mellitus: an implantable glucose sensor with direct electron transfer" *Diabetologia*, 1989, pp. 213-217, vol. 32, No. 3.

Pieper, J.S. et al. "Crosslinked type II collagen matrices: preparation, characterization, and potential for cartilage engineering" *Biomaterials*, 2002, pp. 3183-3192, vol. 23.

Quinn, C.P. et al. "Photo-crosslinked copolymers of 2-hydroxyethyl methacrylate, poly(ethylene glycol) tetra-acrylate and ethylene dimethacrylate for improving biocompatibility of biosensors" *Biomaterials*, 1995, pp. 389-396, vol. 16, No. 5.

Reddy, S.M. et al. "Ion exchanger modified PVC membranes-selectivity studies and response amplification of oxalate and lactate enzyme electrodes" *Biosensors & Bioelectronics*, 1997, pp. 1003-1012, vol. 12, Nos. 9-10.

Rigby, G.P. et al. "Open flow microperfusion: approach to in vivo glucose monitoring" *Med Biol Eng Comput*, Mar. 1995, pp. 231-234, vol. 33, No. 2, abstract.

Sharkawy, A.A. et al. "Engineering the tissue which encapsulates subcutaneous implants. I. Diffusion properties" *J Biomed Mater Res*, 1997, pp. 401-412, vol. 37.

Shaw, G.W. et al. "In vitro testing of a simply constructed, highly stable glucose sensor suitable for implantation in diabetic patients" *Biosensors & Bioelectronics*, 1991, pp. 401-406, vol. 6.

Sheu, M.T. et al. "Characterization of collagen gel solutions and collagen matrices for cell culture" *Biomaterials*, 2001, pp. 1713-1719, vol. 22.

Shichiri, M. et al. "In vivo characteristics of needle-type glucose sensor-measurements of subcutaneous glucose concentrations in human volunteers" *Horm Metab Res Suppl*, 1988, pp. 17-20, vol. 20, abstract.

Sung, H.W. et al. "Cross-linking characteristics of biological tissues fixed with monofunctional or multifunctional epoxy compounds" *Biomaterials*, 1996, pp. 1405-1410, vol. 17, No. 14.

Van Luyn, M.J. et al. "Secondary cytotoxicity of cross-linked dermal sheep collagens during repeated exposure to human fibroblasts" *Biomaterials*, 1992, pp. 1017-1024, vol. 13, No. 14, abstract.

Wilkins, E. et al. "Integrated implantable device for long-term glucose monitoring" *Biosensors & Bioelectronics*, 1995, pp. 485-494, vol. 10, No. 5.

Yu, B. et al. "A long-term flexible minimally-invasive implantable glucose biosensor based on an epoxy-enhanced polyurethane membrane" *Biosensors and Bioelectronics*, 2006, pp. 2275-2282, vol. 21.

Amalvy, J.I. "Semicontinuous emulsion polymerization of methyl methacrylate, ethyl acrylate, and methacrylic acid" *Journal of Applied Polymer Science*, 1996, pp. 339-344, vol. 59.

Capek, I. et al. "Emulsion copolymerization of methyl methacrylate with ethyl acrylate, 1: Effect of the initiator concentration on the polymerization behaviour" *Makromol. Chem.*, 1986, pp. 2063-2072, vol. 187.

Chen, G. et al. "A hybrid network of synthetic polymer mesh and collagen sponge" *Chem. Commun.*, published on the web Jul. 19, 2000, pp. 1505-1506.

Chen, G. et al. "Culturing of skin fibroblasts in a thin PLGA-collagen hybrid mesh" *Biomaterials*, May 2005, pp. 2559-2566, vol. 26, No. 15.

Coombes, A.G.A. et al. "Biocomposites of non-crosslinked natural and synthetic polymers" *Biomaterials*, 2002, pp. 2113-2118, vol. 23.

Rao, K.P. et al. "Collagen-poly(methyl methacrylate) graft copolymers: Effect of aqueous organic solvent system and salts on copolymer composition" *Die Makromolekulare Chemie*, 1974, pp. 729-737, vol. 175.

Venugopal, J. et al. "Fabrication of modified and functionalized polycaprolactone nanofibre scaffolds for vascular tissue engineering" *Nanotechnology*, 2005, pp. 2138-2142, vol. 16.

Yang, S. et al. "The design of scaffolds for use in tissue engineering. Part I. Traditional factors" *Tissue Engineering*, 2001, pp. 679-689, vol. 7, No. 6.

* cited by examiner

FIG. 5B

METHOD FOR PRODUCING BIOCOMPOSITE COMPRISING COLLAGEN AND POLYMER

CROSS-REFERENCE TO RELATED APPLICATION

The present application claims the benefit of U.S. Provisional Application Ser. No. 60/844,290, filed Sep. 13, 2006, which is hereby incorporated by reference herein in its entirety, including any figures, tables, nucleic acid sequences, amino acid sequences, and drawings.

GOVERNMENT SUPPORT

The subject matter of this application has been supported by a research grant from the National Science Foundation under grant number DGE 0221681. Accordingly, the government has certain rights in this invention.

BACKGROUND OF THE INVENTION

Fibrous vertebrate tissues are generally composed of two types of biopolymers that are responsible for the mechanical properties of the tissues: collagen for strength and stiffness, and elastin for extensibility. It would be advantageous to have available a biocomposite material that addresses the problems associated with the current medical practices involving prosthetic materials. Such technology would greatly improve the overall efficiency and affordability of numerous surgeries which involve prosthetics by decreasing the risk of autoimmune response to the prosthesis, increasing the structural soundness of the prosthesis, and by decreasing the risk of post-operative infection at the site of the implant.

BRIEF SUMMARY OF THE INVENTION

The invention concerns a composite material (a "biocomposite") comprising a biotic material and an abiotic material, useful in artificial tissue replacement surgeries. In one embodiment, the biotic material of the biocomposite comprises collagen and the abiotic material comprises a polymer.

In one embodiment, the polymer is a co-polymer such as ethyl acrylate-methyl methacrylate copolymer. In another embodiment, the polymer is either polyacrylate or poly(acrylate-styrene) co-polymer.

The biocomposite can be produced in a variety of regular or irregular forms. In one embodiment, the biocomposite is one or more fibers (also referred to herein as a fibril or fibrillar biocomposite, or a biocomposite fiber).

In an exemplified embodiment described herein, sea cucumber collagen fibrils were combined with polymeric nanoparticles in a water-based solution to form emulsified collagen fibers. These new fibers have improved biomechanical properties over both constituents alone, and display unique features that allow them to have the potential to be utilized in numerous areas of prosthetics, including but not limited to heart valve replacements, artificial skin replacement, and ligament and tendon replacements. Various polymeric nanoparticles and ratios of polymer-to-biotic material (e.g., polymer-to-collagen) can be utilized in order to alter the mechanical properties of the biocomposite (e.g., composite fiber), and mammalian biotic material (e.g., fibers and/or fibrils) can also be incorporated into the system in order to provide a more biocompatible prosthesis.

Another aspect of the invention concerns a method for producing a biocomposite comprising a biotic material and an abiotic material. In one embodiment, the production method comprises polymerizing a biotic material and an abiotic material by radical emulsion polymerization, thereby forming the synthetic biocomposite. The degree of stiffness and elasticity can be easily controlled by varying the ratios of abiotic material to biotic material (e.g., varying the ratios polymer to collagen). In one embodiment, the polymer in the polymer emulsion is a co-polymer such as ethyl acrylate-methyl methacrylate copolymer. In another embodiment, polymer in the polymer emulsion is either polyacrylate or poly(acrylate-styrene) co-polymer. Optionally, the polymers can be synthesized as nanoparticles in an aqueous emulsion.

Another aspect of the invention concerns a method for treating a tissue defect within a human or animal subject, comprising applying an effective amount of a biocomposite of the invention to the site of the tissue defect. The biocomposites of the invention have the potential to improve the efficiency and affordability of surgical procedures involving prosthetics by decreasing the risk of autoimmune response to the prosthesis, increasing the structural integrity of the prosthesis, and by decreasing the risk of post-operative infection at the site of the implant.

Another aspect of the invention concerns a method for delivering a biologically active agent to a target anatomical site in a human or animal subject, comprising applying an effective amount of a biocomposite of the invention to the target site, wherein the biocomposite includes a biologically active agent. For example, the biologically active agent can comprise at least one member selected from the group consisting of medicaments; vitamins; mineral supplements; substances used for the treatment, prevention, diagnosis, cure or mitigation of disease or illness; substances affecting the structure or function of the body; drugs; antimicrobial agents; antifungal agents; antibacterial agents; antiviral agents; antiparasitic agents; growth factors; angiogenic factors; anaesthetics; mucopolysaccharides; metals; cells; acid mucopolysaccharides; proteins; enzymes, peptides; and wound healing agents.

BRIEF DESCRIPTION OF THE DRAWINGS

FIGS. 2A and 2B show TEM of a cross-section of control collagen fiber (FIG. 2A) and KRG3-treated fiber (FIG. 2B). The control fiber contains mainly linearly-arranged fibrils tightly packed in the fiber in a longitudinal orientation. The emulsion-treated fibrils do not appear to have a linear arrangement and are also much more loosely arranged within the fiber. The spatial difference in the composite fiber is due to the intertwining of the emulsion with the fibrils during fiber formation. The random orientation is most likely a factor of the mixing performed when the emulsion is introduced.

DETAILED DESCRIPTION OF THE INVENTION

The present invention concerns a synthetic biocomposite comprising a biotic material and an abiotic material, which is useful in artificial tissue replacement; methods for its production; and methods of use. In one embodiment, the biotic material of the biocomposite comprises collagen and the abiotic material comprises a polymer. The biocomposite can be implanted into humans or animals as an artificial tissue. The biocomposite can be formed or manipulated into a desired shape for implantation.

As described in the Examples section, radical emulsion polymerization was employed to synthesize an ethyl acrylate-methyl methacrylate copolymer, which, when in solid film form, displays mechanical properties comparable to elastin. The polymerization was performed under a nitrogen environment at 70° C. and utilizes a two-step synthesis. First, the acrylate monomers were emulsified in 80% water and 3% surfactant, then the acrylates are co-polymerized through the use of a radical initiator. The resulting nanoparticle-based emulsion was then mixed in various ratios with native sea cucumber collagen fibrils suspended in water and placed in dialysis bags. The dialysis bags were then placed in 3% acetic acid overnight for fiber formation, then the fibers are removed from the bags and allowed to air dry. The dry fibers are then cut into pieces of approximately 15 mm in length for mechanical analysis. The composite fibers displayed the most advantageous property of each constituent: they preserve the high tensile strength of collagen while sustaining the long range elasticity of the polymer films. The degree of fiber stiffness and elasticity is easily controlled by varying the ratios of polymer to collagen. Biocompatibility of the polymer was established in vitro against human dermal fibroblasts. Therefore, the polymer/collagen composite fibers may be used as biocompatible materials for artificial tissue. In one embodiment, the biocomposite is doped with an inorganic mineral, such as calcium.

In one embodiment, the biocomposite is intercalated, e.g., with the abiotic material intercalated into at least a portion of the biotic material, or vice-versa. As shown by embodiments in FIGS. 2A and 2B, the polymer and the collagen fibrils are intertwined, with the fibrils in a random (non-linear orientation), representative of intercalation of the abiotic material (polymer) into the biotic material (collagen). As shown in FIGS. 3A-3D, the biocomposites can be produced and maintained in hydrated or dehydrated form. The biocomposite is capable of retaining its mechanical properties in a moist environment.

One aspect of the invention concerns a method for producing a synthetic biocomposite, comprising polymerizing a biotic material and an abiotic material by emulsion polymerization (e.g., radical emulsion polymerization), thereby forming the synthetic biocomposite. Emulsion polymerization is a popular and well-known polymerization method (Esumi, K., *Polymer Interfaces and Emulsions*, Marcel Dekker, New York, 1999; Gilbert, R. G. *Emulsion Polymerization: a Mechanistic Approach* Academic Press, London, 1996; Anderson C. D. and Daniels E. S., Emulsion Polymerization and Latex Applications, Rapra Review Reports, volume 14, report 160; Odian, *Principles of Polymerization*, $3^{rd}$ Ed., John Wiley and Sons, Inc., New York, 1991; Rosen, S. L., *Fundamental Principles of Polymeric Materials"*, $2^{nd}$ Ed., John Wiley and Sons, Inc., New York, 1993, which are each incorporated herein by reference in their entirety). Reactants that are necessary or useful in carrying out emulsion polymerization reactions, such as monomers, comonomers, initiators, surfactants (emulsifiers), non-surfactant stabilizers, chain transfer agents, buffering agents, inert salts, and preservatives (e.g., to retard bacterial growth) are known in the art and can be employed in carrying out the production method of the invention. The degree of stiffness and elasticity can be easily controlled by varying the ratios of abiotic material to biotic material (e.g., varying the ratios polymer to collagen). In one embodiment, the polymer in the polymer emulsion is a co-polymer such as ethyl acrylate-methyl methacrylate copolymer. In another embodiment, polymer in the polymer emulsion is either polyacrylate or poly(acrylate-styrene) co-polymer. Optionally, the polymers can be synthesized as nanoparticles in an aqueous emulsion.

Any monomer can be used for a polymer component (e.g., the abiotic component) of the biocomposite and production methods of the invention. Preferably, the monomer utilized is an acrylic monomer, a vinyl monomer, or a modified resin of either. Monomers utilized for the abiotic component in the subject invention can include, but are not limited to, acrylonitrile, acrylic acid, maleic acid, methyl acrylate, ethyl acrylate, butyl acrylate, butyl methacrylate, 2-ethylhexyl acrylate, methoxyethyl acrylate, dimethylamino acrylate, methacrylic acid, isobutyl methacrylate, 2-ethyl hexyl methacrylate, lauryl methacrylate, stearic methacrylate, dimethyl amino methacrylate, allyl methacrylate, 2-hydroxyethyl acrylate, 2-hydroxy propyl acrylate, 2-hydroxy ethyl methacrylate, modified acrylamide, modified methacrylamide glycidyl acrylate, styrene, vinyl acetate, vinyl toluene, and synthetically modified acrylics. Preferably, the monomer is ethyl acrylate. In one embodiment, the polymer is a co-polymer such as ethyl acrylate-methyl methacrylate copolymer. In another embodiment, the polymer is either polyacrylate or poly(acrylate-styrene) co-polymer.

The free-radicals that can be utilized in the production methods of the subject invention include, but are not limited to, peroxides; persulphates; alkyl hydroperoxides; sodium, ammonium, and potassium salts of persulphate; thiosulphates; metabisulphites; and hydrosulphides. The initiator must be water soluble, and the free radicals may be generated thermally or by use of an oxidation-reduction (or redox) couple. The major initiators used in emulsion polymerization are persulphates. Even though initiating efficiency and half life of persulphates vary, ammonium persulphate is preferred in practice because of its better solubility. Hydroperoxides are often used particularly as a post reaction initiator to kill the unreacted monomers after emulsion polymerization.

The rate of free radical generation increases with temperature, and it is normal to employ reaction temperatures of 60-90° C. when using thermal generation techniques. However, when redox couples (thiosulphates, metabissulphites, and hydrosulphides) are employed, the rate of free radical generation is increased to that provided by thermal generation at the same temperature. Therefore, when using redox couples, reaction temperatures can be made as low as 30° C., or even room temperature. The free radicals can be added as an aqueous solution repeatedly until a milky solution is formed.

The aqueous media utilized in any pre-emulsifying and initiating steps can include de-ionized water or nano-pure water. As known to those skilled in the art, a buffer solution may be necessary depending on the surfactant and stabilization.

The type of reaction vessel or vessels utilized for producing the biocomposites of the invention, and the sizes of the vessels, are not critical. Any vessel or substrate capable of holding or supporting the reactants so as to allow the reaction to take place can be used. It should be understood that, unless expressly indicated to the contrary, the terms "adding", "contacting", "mixing", "reacting", "combining" and grammatical variations thereof, are used interchangeable to refer to the mixture of reactants of the process of the present invention (e.g., monomer, biotic material, polymerization initiator, surfactant, and so forth), and the reciprocal mixture of those reactants, one with the other (i.e., vice-versa).

The biocomposites can be made in the form of single fibers, fibrous mats (fibers may be in various ordered (e.g., woven or parallel) or random orientations with respect to one another), particles, sheets, films, etc.

In one aspect, the invention concerns a synthetic biocomposite comprising a biotic material and an abiotic material. In one embodiment, the biotic material is collagen and the abiotic material is a polymer. In another embodiment, the biocomposite is an abiotic fiber comprising intertwined polymer emulsion and fibrils, such as collagen fibrils. In another embodiment, the abiotic material is a polymer emulsion.

In one embodiment, the biotic material of the biocomposite is fibrous. As used herein, the term "fibrous" is intended to refer to matrices having at least some fiber (high aspect ratio) component. The fibers can be of various lengths, diameters, and orientations (e.g., parallel, mesh, random). The terms "fibers" and "fibrils" are used interchangeably herein to refer to filamentous or thread-like matter and any sub-fibers that contribute to a larger fiber. Fibrils may also represent sub-fibers of a larger fiber. The fibers can be produced by self-assembly or directed assembly of molecules through synthesis procedures. Other fibrous matrices can be found, for example, in Vincent, J. (Structural Biomaterials, Princeton University Press, Princeton, N.J., 1990, Chapter 3, pp. 73-91).

Another aspect of the invention is a device comprising a surface with the synthetic biocomposite of the invention. In one embodiment, the device is a medical device intended for implantation in to a human or animal subject. In another embodiment, the device is fibrous scaffold for cell or tissue engineering.

Another aspect of the invention is a method for treating a tissue defect, comprising applying a synthetic biocomposite of the invention to the site of the defect.

Another aspect of the invention is a method for producing a synthetic biocomposite, comprising polymerizing a biotic material and an abiotic material by radical emulsion polymerization, thereby forming the synthetic biocomposite. The type of reaction vessel or vessels utilized for producing the biocomposites of the invention, and the sizes of the vessels, are not critical. Any vessel or substrate capable of holding or supporting the reactants so as to allow the reaction to take place can be used. It should be understood that, unless expressly indicated to the contrary, the terms "adding", "contacting", "mixing", "reacting", "combining" and grammatical variations thereof, are used interchangeable to refer to the mixture of reactants of the process of the present invention (e.g., biotic material, abiotic material, biologically active agent, and so forth), and the reciprocal mixture of those reactants, one with the other (i.e., vice-versa).

An aspect of the invention concerns a method for treating a tissue defect within a subject, comprising applying an effective amount of a biocomposite of the invention to the site of the tissue defect. As used herein, the term "subject" refers to any human or non-human animal (e.g., mammal), such as one suffering from a tissue defect. According to the method of the subject invention, a therapeutically effective amount of the biocomposite can be applied at the site of a tissue defect to partially or fully restore structural integrity to the tissue. Once applied, the biocomposite of the subject invention can function as a filler (or partial filler) or plug, to mend the tissue defect. The amount to be applied will depend upon the size and nature of the tissue defect, and the clinical outcome that is sought. The biocomposite can be applied in a malleable form, for example, as a paste or putty, such that the administered composition takes the shape of the bone defect. Alternatively, the biocomposite can be molded pre-cast into a desired shape (such as the shape of the defect) using polymer composition molding methods known to those of ordinary skill in the art, and the molded composition can be administered as a solid or semi-solid article. Thus, the size, volume, thickness, and shape of the molded article can be controlled, as desired. The biocomposite can be applied in particulate form. According to the method of the subject invention, the biocomposite can be applied so that it directly contacts existing tissue adjacent to, or defining, the tissue defect site, or the biocomposite can be contacting another implant, or both.

The biocomposites of the subject invention can be applied to the tissue defect site as a in any physical state (solid, liquid, semi-solid, etc.). Preferably, the biocomposite is applied as a liquid. Once applied, with a syringe for example, the liquid composition can coagulate or cure ("set") shortly after application to form a solid.

The biocomposite of the subject invention (and compositions comprising the biocomposite) can be used as a vehicle for the in situ delivery of biologically active agents. The biologically active agents incorporated into, or included as an additive within, the biocomposite of the invention can include, without limitation, medicaments, growth factors, vitamins, mineral supplements, substances used for the treatment, prevention, diagnosis, cure or mitigation of disease or illness, substances which affect the structure or function of the body, or drugs. The biologically active agent can take several forms, such as polypeptides, nucleic acid molecules (DNA, RNA, etc.), small chemical molecules, carbohydrates, etc. The biologically active agents can be used, for example, to facilitate implantation of the biocomposite into a patient and to promote subsequent integration and healing processes. The active agents include, but are not limited to, antifungal agents, antibacterial agents, anti-viral agents, anti-parasitic agents, growth factors, angiogenic factors, anaesthetics, mucopolysaccharides, metals, cells, and other wound healing agents. Because the processing conditions can be relatively benign (physiological temperature and pH), live cells can be incorporated into fiber constructs during their formation, or subsequently allowed to infiltrate the fibers or compositions through tissue engineering techniques.

As indicated above, cells can be seeded on to and/or within the biocomposites of the present invention. The cells can be in any state of differentiation, such as undifferentiated adult or embryonic stem cells, progenitor cells, or differentiated cells. Likewise, tissues such as cartilage can be associated with the biocomposite prior to implantation within a subject. Examples of such cells include, but are not limited to, bone cells (such as osteoclasts, osteoblasts, and osteocytes), blood cells, epithelial cells, neural cells (e.g., neurons, astrocytes, and oligodendrocytes), and dental cells (odontoblasts and ameloblasts). Seeded cells can be autogenic, allogenic, or xenogenic to the biotic material of the biocomposite and/or the subject to which the biocomposite is to be administered. Seeded cells can be encapsulated or non-encapsulated.

Examples of antimicrobial agents that can be incorporated into and/or on the biocomposite of the invention (or in compositions comprising the biocomposite) include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericine B, ketoconazole, fluconazole, pyrimethamine, sulfadiazine, clindamycin, lincomycin, pentamidine, atovaquone, paromomycin, diclarazaril, acyclovir, trifluorouridine, foscarnet, penicillin, gentamicin, ganciclovir, iatroconazole, miconazole, Zn-pyrithione, and silver salts, such as chloride, bromide, iodide, and periodate.

Growth factors that can be incorporated into and/or on the biocomposite of the invention (or in compositions comprising the biocomposite) include, but are not limited to, bone growth factors (e.g., BMP, OP-1) basic fibroblast growth factor (bFGF), acidic fibroblast growth factor (aFGF), nerve growth factor (NGF), epidermal growth factor (EGF), insulin-like growth factors 1 and 2 (IGF-1 and IGF-2), platelet-derived growth factor (PDGF), tumor angiogenesis factor (TAF), vascular endothelial growth factor (VEGF), corticotropin releasing factor (CRF), transforming growth factors alpha and beta (TGF-.alpha. and TGF-.beta.), interleukin-8 (IL-8), granulocyte-macrophage colony stimulating factor (GM-CSF), the interleukins, and the interferons.

Other agents that can be incorporated into the biocomposites or compositions containing them include acid mucopolysaccharides including, but not limited to, heparin, heparin sulfate, heparinoids, dermatan sulfate, pentosan polysulfate, chondroitin sulfate, hyaluronic acid, cellulose, agarose, chitin, dextran, carrageenin, linoleic acid, and allantoin.

Proteins that can be incorporated into, or included as an additive within, the biocomposite or compositions comprising the biocomposite include, but are not limited to, collagen (including cross-linked collagen), fibronectin, laminin, elastin (including cross-linked elastin), osteopontin, osteonectin, bone sialoproteins (Bsp), alpha-2HS-glycoproteins, bone Gla-protein (Bgp), matrix Gla-protein, bone phosphoglycoprotein, bone phosphoprotein, bone proteoglycan, protolipids, bone morphogenetic protein, cartilage induction factor, platelet derived growth factor and skeletal growth factor, enzymes, or combinations and biologically active fragments thereof. Other proteins associated with other parts of human or other mammalian anatomy can be incorporated or included as an additive, including proteins associated with cartilage, such as chondrocalcining protein, proteins associated with dentin, such as phosphoryin, glycoproteins and other Gla proteins, or proteins associated with enamel, such as amelogenin and enamelin. Agents incorporated into the biocomposites or compositions of the subject invention may or may not facilitate or enhance osteoinduction. Adjuvants that diminish an immune response can also be used in conjunction with the fibers or compositions of the subject invention.

The bioactive molecule need not be a therapeutic agent. For example, the bioactive molecule may be cytotoxic to the local cells to which it is delivered but have an overall beneficial effect on the subject. Further, the bioactive molecule may be a diagnostic agent with no direct therapeutic activity per se, such as a contrast agent for bioimaging.

A description of these classes of drugs and diagnostic agents and a listing of species within each class can be found, for example, in Martindale, The Extra Pharmacopoeia, Twenty-ninth Edition (The Pharmaceutical Press, London, 1989), which is incorporated herein by reference in its entirety. Drugs or diagnostic agents are commercially available and/or can be prepared by techniques known in the art.

The biologically active agents can first be encapsulated into microcapsules, microspheres, microparticles, microfibers, reinforcing fibers and the like to facilitate mixing and achieving controlled, extended, delayed and/or sustained release. Encapsulating the biologically active agent can also protect the agent against degradation during formation of the biocomposites or compositions of the invention.

Additionally, the biologically active agents can be pendantly attached to the biocomposite. The attachment can be facilitated through covalently linking the agent to a component of the biocomposite, or through the use of hydrogen bonding.

In preferred embodiments of the invention, the biologically active agent is controllably released into a human or animal subject when the biocomposite or composition of the invention is implanted into the subject, either through degradation in the aqueous environment, or more preferably, due to bioresorption relying on the time scale resulting from cellular remodeling. The biocomposites of the subject invention can be used to replace an area of discontinuity in the tissue in the subject's body. The area of discontinuity in the tissue can be as a result of trauma, disease, genetic defect, tumor, or surgery, for example.

The biocomposites of the invention can be incorporated into medical devices. As used herein, a "medical device" may be defined as a device that has surfaces that contact blood or other bodily tissues in the course of their operation. This can include, for example, extracorporeal devices for use in surgery such as blood oxygenators, blood pumps, blood sensors, tubing used to carry blood and the like which contact blood which is then returned to the patient. This can also include implantable devices such as artificial skin (skin grafts), vascular grafts, stents, electrical stimulation leads, heart valves, bladder products (e.g., for augmentation or replacement of a malfunctioning bladder due to congenital deficiencies, resections following cancer, trauma, or other genitourinary conditions), orthopedic devices, catheters, shunts, sensors, replacement devices for nucleus pulposus, cochlear or middle ear implants, intraocular lenses, and the like.

The biocomposite of the subject invention can be formulated into a variety of shapes suitable for its function as a medical device, such as a plate, pin, rod, tube, coil, screw, anchor, tack, arrow, staple, button, or other regular or irregular shape. The biocomposite of the present invention can be formulated as a three-dimensional scaffold and, optionally, seeded with one or more cell types for implantation within a human or animal subject. In embodiments of a prosthesis in which the biotic material is collagen, for example the invention allows formation of a prosthesis in any shape or size. The bulk collagen (e.g., bovine tendon collagen) can be solubilized by digestion with a protease (e.g., papain). The soluble collagen is then extruded into a synthetic fiber or otherwise shaped, where spontaneous formation of fibrils lends weak integrity to the prosthesis.

As indicated above, the abiotic material can be a polymer. The biotic material can also be a polymer (a polymer of biological origin, e.g., a protein such as collagen). In those embodiments in which the biotic material of the biocomposite comprises collagen, various types of collagens from various sources may be utilized. Collagen type 1, collagen type 2, collagen type 3, collagen type 4, collagen type 5, collagen type 6, collagen type 7, collagen type 8, collagen type 9, collagen type 10, collagen type 11, collagen type 12, collagen type 13, collagen type 14, collagen type 15, collagen type 16, collagen type 17, collagen type 18, collagen type 19, and collagen type 20, or combinations thereof can be utilized, for example (Kadler et al., *Biochem. J*, 1996, 316:1-11; Badylak, *Cell & Developmental Biology*, 2002, 13:377-383; and Gelse et al., *Advanced Drug Delivery Reviews*, 2003, 55:1531-1546). Other polymers of biological origin that may be utilized include, for example, gelatin (including denatured gelatin), alginates, chitosan, silk, and cellulose. Other examples of biotic and abiotic polymeric materials that may be utilized for the biocomposite of the invention are described in U.S. Pat. No. 6,565,960 (Koob et al.), which is incorporated herein by reference in its entirety.

In embodiments in which the biotic material is a collagen, suitable collagens can be any form of a collagen polypeptide. For example, the species origin of the collagen polypeptide can be from any eukaryotic organism, including invertebrates (e.g., sea cucumbers, starfish, sea urchins, worms, and sponges) and vertebrates (e.g., hagfish, sharks, skates and rays, bony fish, and mammals such as monkeys, chickens, pigs, and cows), and from any tissue, including skin, tendon, cartilage, or ligament. Also suitable are collagen polypeptides produced recombinantly (e.g., in a human cell line, bacterium, or yeast). In addition, the collagen can be, but need not be, free of any tertiary or quaternary structure, such as in gelatin, a denatured form of collagen.

In another embodiment, if collagen is to be utilized, the collagen can be in the form of a complex biological structure, such as in a freshly harvested tendon fiber. Where the collagen is already formed into a complex structure, it may be necessary to incubate the collagen in the presence of the compound before oxidation and polymerization to allow the compound to infiltrate the collagen.

The biocomposites are useful in a variety of methods for making materials for biomedical and other applications. The biocomposite can be applied as a bandage, or incorporated in to a bandage, for application to an acute or chronic wound.

Other aspects of the invention relate to the polymer compositions, methods of making them, and methods of improving characteristics of the polymeric materials relevant for biomedical applications (e.g., tensile strength, biocompatibility, biodegradation (or lack thereof), porosity (e.g., for cell infiltration and tissue engineering), elasticity, compressive strength, thermal stability, moldability, or non-antigenicity, etc.) using the compounds and methods herein.

The abiotic material of the composite can be a gel. Gelatin gels are particularly useful for in vivo applications. Hydrogels can be used alone or in combination with other materials such as glycosaminoglycans and collagen fibrils for applications including, for example, as a space filling biomaterial for reconstructive surgery (e.g., cranial and facial reconstruction), a biomimetic cartilage for repair of focal lesions, a resorbable carrier for phased release of cytokines such as bone morphogenetic proteins (BMPs) for bone repair, or a patterning scaffold for musculoskeletal regeneration.

Gelatin in liquid form can be used as well. Typically, gelatin remains a viscous fluid at 37° C. Thus, use of liquid gelatin for biomedical applications in vivo is not possible when the application requires compressive load capacity or other strength property (e.g., tensile strength or elasticity) of the material. For example, it can be used as an injectable space filling material for reconstructive surgery (e.g., cranial or facial), injected to fill voids without surgical intervention, it can be molded to irregular shapes for tissue augmentation during reconstructive surgery, or it can form a polymerizable scaffold in which to deliver and then immobilize cells, cytokines or therapeutic agents.

Gelatin foams (e.g., GELFOAM, available from Pharmacia, Peapack, N.J.) are an additional area for application of the biocomposite and methods of the invention. Gelatin foams are useful as delivery systems for therapeutic agents, cytokines, and musculoskeletal cells, particularly mesenchymal stem cells. The potential use of the gelatin foam in tissue engineering is suspect because it is extremely friable and lacks compressive stiffness and resilience.

In addition to their therapeutic applications, the biocomposites of the present invention may be used as scaffolds on which to grow cells in vitro, or as filler in plastics, paint, coatings, and paper production.

U.S. Pat. No. 6,565,960 (Koob et al.) is incorporated herein by reference in their entirety. U.S. Patent Application Publication No. US2007/019160A1 (Turos et al.) and PCT Publication No. WO 2005/020933 (Turos et al.) are incorporated herein by reference in their entirety.

Measuring Beneficial Properties

If the biocomposites of the invention are to be implanted or otherwise applied or administered in the body of a subject, the composition should be biocompatible. To assess biocompatibility, cells (e.g., a fibroblast cell line) can be seeded onto the composition in a culture dish. If the fibroblasts are able to replicate and attach to the composition, the composition is likely to be biocompatible. Alternatively, the composition can be implanted into the body of a subject (e.g., a mouse, rat, dog, pig, or monkey) for a specified time, then removed to evaluate the number and/or health of the cells attached to the composition. The ability of the biocomposite to support growth of fibroblasts is particularly important when infiltration of cells and deposition of an extracellular matrix on the composition are desired in vivo.

Biocompatibility can also be assessed by evaluating the immune response, or lack thereof, against the composition. A suitable in vitro test is to contact human monocyte/macrophages to the biocomposite, which can be in the form of small particles of about 1 to 10 μm in diameter for testing. The monocyte/macrophage culture is then examined for signs of an inflammatory response, including (1) phagocytosis of the biocomposite particles, (2) increased lysozomal activity, and/or (3) increased prostaglandin $E_2$ in the culture. For in vivo testing, the biocomposite can be implanted into an animal (e.g., a rabbit), and the animal monitored for signs of, for example, increased lymphocyte, neutrophil, or macrophage cell number locally or systemically; increased concentrations of cytokines locally or systemically; fever; and immune cell infiltration of the composition. The quantitation of specific cell types, such as monocytes, helper T cells, and B cells, is accomplished using standard methods such as fluorescence-assisted cell sorting. In addition, B cell activation can be evaluated by culturing B cells from the animal in which the biocomposite had been implanted, contacting the B cells with the biocomposite, and determining whether the B cells proliferate in response to the biocomposite. Other standard methods for evaluating an immune response in an animal can be used.

Another measure of biocompatibility that can be utilized is the susceptibility of the biocomposite to proteolytic digestion in vivo. The desired level of protease resistance depends on the intended use of the composition. For measuring the level of protease resistance of the biocomposite, the biocomposite can be incubated with a protease (e.g., collagenase or papain)

for a specified amount of time, then evaluated for any decrease in a physical property (e.g., tensile strength) of the biocomposite or the presence of any degradation product of the biotic material (e.g., collagen) or abiotic material (e.g., polymer).

Physical Properties

The biocomposites of the invention can exhibit beneficial physical properties, such as high tensile strength, high stiffness (or elastic modulus), and low strain at failure. A high tensile strength is desirable in, e.g., a prosthetic tendon, to avoid rupture of the prosthesis under stress in vivo, such as when the muscle to which the prosthesis is attached is contracted. Similarly, a high stiffness is necessary to stabilize the relative positions of the parts (e.g., muscle to bone) to which the prosthesis is attached. A high stiffness means that a synthetic fiber, for example does not stretch much under applied loads, which is important for a tendon because nearly all of the force from a muscle is transferred to the insertion site with little loss of energy in extending the tendon. Moreover, the proper full excursion of the limb as the muscle contracts requires that the tendon does not extend. A low strain at failure indicates that the fiber does not extend under load before failure. High tensile strength with no fiber stretching will provide the most efficient transfer of energy from the muscle to the bone insertion. To measure these physical properties, any suitable apparatus having (1) two clamps for attaching to the prosthesis, (2) a force transducer attached to one of the clamps for measuring the force applied to the prosthesis, (3) a means for applying the force, and (4) a means for measuring the distance between the clamps, is suitable. Tensiometers are commercially available. To calculate the tensile strength, the force at failure is divided by the cross-sectional area of the prosthesis through which the force is applied, resulting in a value that can be expressed in force (e.g., Newtons) per area. The stiffness is the slope of the linear portion of the stress/strain curve. Strain is the real-time change in length during the test divided by the initial length of the specimen before the test begins. The strain at failure is the final length of the specimen when it fails minus the initial specimen length, divided by the initial length.

An additional physical property that is associated with the extent of cross-linking in a composition is the shrinkage temperature. In general, the higher the temperature at which a collagenous composition begins to shrink, the higher the level of cross-linking. The shrinkage temperature of a fiber can be determined by immersing the fiber in a water bath, raising the temperature of the water bath, and observing the temperature of the water bath at which the fiber shrinks. Tension on the fiber may be required for observing the shrinkage. The shrinking temperature for the compositions of the invention can be at least about 60° C. (e.g., at least 65 or 70° C.).

For biocomposites or compositions comprising them that are not elongated in shape, such as in a disk, the fracture pressure can be an indication of physical strength. The fracture pressure is the minimum force per area at which a material cracks.

EXEMPLIFIED EMBODIMENTS

The invention includes, but is not limited to, the following embodiments:

Embodiment 1. A synthetic biocomposite comprising a biotic material and an abiotic material.

Embodiment 2. The biocomposite of embodiment 1, wherein the biotic material is collagen and the abiotic material is a polymer.

Embodiment 3. The biocomposite of embodiment 1, wherein the biocomposite is a fiber comprising an intertwined polymer emulsion and fibrils.

Embodiment 4. The biocomposite of embodiment 3, wherein the fibrils are collagen fibrils.

Embodiment 5. The biocomposite of embodiment of any of embodiments 1-3, wherein the abiotic material is intercalated into the biotic material, or vice-versa.

Embodiment 6. The biocomposite of any preceding embodiment, wherein the abiotic material is a polymer emulsion.

Embodiment 7. The biocomposite of any preceding embodiment, wherein the abiotic material comprises a copolymer emulsion.

Embodiment 8. The biocomposite of embodiment 7, wherein the copolymer is ethyl acrylate-methyl methacrylate.

Embodiment 9. The biocomposite of embodiment 1, wherein the abiotic material is polyacrylate or poly(acrylate-styrene) copolymer.

Embodiment 10. The biocomposite of any preceding embodiment, further comprising a biologically active agent.

Embodiment 11. The biocomposite of embodiment 10, wherein the biologically active agent is a cell.

Embodiment 12. A device comprising a surface with the synthetic biocomposite of any of embodiments 1-11 thereon.

Embodiment 13. The device of embodiment 12, wherein the device is a medical implant.

Embodiment 14. A method for producing a synthetic biocomposite, comprising polymerizing a biotic material and an abiotic material by radical emulsion polymerization, thereby forming the synthetic biocomposite.

Embodiment 15, wherein the biocomposite is one according to any of embodiments 1-11.

Embodiment 16. The method of embodiment 14, wherein the biotic material is collagen and the abiotic material is a polymer.

Embodiment 17. The method of embodiment 14, wherein the biocomposite is an abiotic fiber comprising intertwined polymer emulsion and fibrils.

Embodiment 18. The method of embodiment 17, wherein the fibrils are collagen fibrils.

Embodiment 19. The method of any of embodiments 14-18, wherein the abiotic material is a polymer emulsion.

Embodiment 20. The method of any of embodiments 14-19, wherein the abiotic material comprises a copolymer emulsion.

Embodiment 21. The method of embodiment 20, wherein the copolymer is ethyl acrylate-methyl methacrylate.

Embodiment 22. The method of any of embodiments 14-21, further comprising a biologically active agent.

Embodiment 23. The method of embodiment 22, wherein the biologically active agent is a cell.

Embodiment 24. A method for treating a tissue defect, comprising applying a synthetic biocomposite at the site of the defect, wherein the biocomposite comprises a biotic material and an abiotic material.

Embodiment 25. The method of embodiment 24, wherein the biocomposite is one of embodiments 1-11.

DEFINITIONS

The term "tissue defect", as used herein refers to any tissue deficient region, such as a void, gap, recess, or other discontinuity in the hard or soft tissues. The tissue defect can be artificially or naturally established, and can occur due to disease or trauma, for example. Thus, the tissue defect can occur as a consequence of pathologic, inflammatory, or tumor diseases, surgical interventions, congenital defects, or bone fractures, and the like. Typically, tissue defects in dental applications will be on or within the gum or jaw of the patient's mouth. For example, in the case of certain diseases, such as tumors, the tissue defect is artificially established by removing the tumor tissue. Thus, according to the method of the subject invention, the biocomposite or compositions comprising the biocomposite can be applied, for example, to repair periodontal defects, for craniofacial reconstruction, joint reconstruction, fracture repair, to conduct orthopedic surgical procedures, and spinal fusion, for example. The term "tissue defect" is also intended to include anatomical sites where augmentation to a tissue feature is desired by the patient in the absence of disease or trauma, such as in elective cosmetic surgery. Thus, the "defect" can be one that is subjectively perceived by the patient, and where augmentation of the bone deficient region is desired.

The terms "comprising", "consisting of", and "consisting essentially of" are defined according to their standard meaning and may be substituted for one another throughout the instant application in order to attach the specific meaning associated with each term.

As used in this specification and the appended claims, the singular forms "a", "an", and "the" include plural reference unless the context clearly dictates otherwise. Thus, for example, a reference to "a fiber" includes more than one such fiber, and the like. Reference to "a polymer" includes more than one such polymer. Reference to "a cell" includes more than one such cell. Reference to "a biologically active agent" includes more than one such agent.

As used herein, the term "drug" is interchangeable with the term "biologically active agent" and refers to any agent capable of having a physiologic effect (e.g., a therapeutic or prophylactic effect) on a biosystem such as prokaryotic or eukaryotic cells or organisms, in vivo or in vitro, including, but without limitation, chemotherapeutics, toxins, radiotherapeutics, radiosensitizing agents, gene therapy vectors, antisense nucleic acid constructs, interfering RNA molecules (e.g., siRNA or shRNA), transcription factor decoys, imaging agents, diagnostic agents, agents known to interact with an intracellular protein, polypeptides, and polynucleotides. Drugs that may be utilized in the biocomposites include any type of compound including antibacterial, antiviral, antifungal, or anti-cancer agents. The drug is preferably a water-insoluble or water-soluble solid or a highly viscous liquid.

The drug can be selected from a variety of known classes of drugs, including, for example, analgesics, anesthetics, anti-inflammatory agents, anthelmintics, anti-arrhythmic agents, antiasthma agents, antibiotics (including penicillins), anti-cancer agents (including Taxol), anticoagulants, antidepressants, antidiabetic agents, antiepileptics, antihistamines, antitussives, antihypertensive agents, antimuscarinic agents, antimycobacterial agents, antineoplastic agents, antioxidant agents, antipyretics, immunosuppressants, immunostimulants, antithyroid agents, antiviral agents, anxiolytic sedatives (hypnotics and neuroleptics), astringents, bacteriostatic agents, beta-adrenoceptor blocking agents, blood products and substitutes, bronchodilators, buffering agents, cardiac inotropic agents, chemotherapeutics, contrast media, corticosteroids, cough suppressants (expectorants and mucolytics), diagnostic agents, diagnostic imaging agents, diuretics, dopaminergics (antiparkinsonian agents), free radical scavenging agents, growth factors, haemostatics, immunological agents, lipid regulating agents, muscle relaxants, proteins, peptides and polypeptides, parasympathomimetics, parathyroid calcitonin and biphosphonates, prostaglandins, radiopharmaceuticals, hormones, sex hormones (including steroids), time release binders, anti-allergic agents, stimulants and anoretics, steroids, sympathomimetics, thyroid agents, vaccines, vasodilators, and xanthines.

The biologically active agent need not be a therapeutic agent. For example, the agent may be cytotoxic to the local cells to which it is delivered but have an overall beneficial effect on the subject. Further, the biologically active agent may be a diagnostic agent with no direct therapeutic activity per se, such as a contrast agent for bioimaging.

A description of these classes of drugs and diagnostic agents and a listing of species within each class can be found, for instance, in Martindale, The Extra Pharmacopoeia, Twenty-ninth Edition (The Pharmaceutical Press, London, 1989), which is incorporated herein by reference in its entirety. The drugs or diagnostic agents are commercially available and/or can be prepared by techniques known in the art.

Poorly water soluble drugs which may be suitably used in the practice of the subject invention include but are not limited to alprazolam, amiodarone, amlodipine, astemizole, atenolol, azathioprine, azelatine, beclomethasone, budesonide, buprenorphine, butalbital, carbamazepine, carbidopa, cefotaxime, cephalexin, cholestyramine, ciprofloxacin, cisapride, cisplatin, clarithromycin, clonazepam, clozapine, cyclosporin, diazepam, diclofenac sodium, digoxin, dipyridamole, divalproex, dobutamine, doxazosin, enalapril, estradiol, etodolac, etoposide, famotidine, felodipine, fentanyl citrate, fexofenadine, finasteride, fluconazole, flunisolide, flurbiprofen, fluvoxamine, furosemide, glipizide, gliburide, ibuprofen, isosorbide dinitrate, isotretinoin, isradipine, itraconazole, ketoconazole, ketoprofen, lamotrigine, lansoprazole, loperamide, loratadine, lorazepam, lovastatin, medroxyprogesterone, mefenamic acid, methylprednisolone, midazolam, mometasone, nabumetone, naproxen, nicergoline, nifedipine, norfloxacin, omeprazole, paclitaxel, phenyloin, piroxicam, quinapril, ramipril, risperidone, sertraline, simvastatin, sulindac, terbinafine, terfenadine, triamcinolone, valproic acid, zolpidem, or pharmaceutically acceptable salts of any of the above-mentioned drugs.

The terms "biosystem", "host", "host biosystem", "patient", "recipient", and "subject", are used interchangeably and, for the purposes of the present invention, include both prokaryotic and eukaryotic cells, such as human cells and non-human animal cells (e.g., mammal cells). Biocomposites of the subject invention may be applied, administered, or otherwise contacted to such cells in vitro or in vivo. Thus, the methods of administration are applicable to both human therapy and veterinary applications, as well as research applications in vitro or within animal models.

As used herein, an "effective amount" of biocomposite or of biologically active agent is that amount effective to bring about the physiological changed desired in the biosystem to which the biocomposite is administered. The term "therapeutically effective amount" as used herein, means that amount of biocomposite or of biologically active agent, alone or in combination with another agent according to the particular aspect of the invention, that elicits the biological or medicinal response in a biosystem that is being sought by a researcher, veterinarian, medical doctor or other clinician, which includes alleviation of the symptoms of the disease or disorder being treated.

For example, if the biologically active agent is a therapeutic agent, an effective amount of the biocomposite comprising the biologically active agent can be that amount sufficient to treat a pathological condition (e.g., a disease or other disorder, a tissue defect) in the biosystem to which the biocomposite is administered. For example, in the case of cancer, the therapeutically effective amount of the biologically active agent may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve, to some extent, one or more of the symptoms associated with the cancer. To the extent the agent may prevent growth and/or kill existing cancer cells, it may be cytostatic and/or cytotoxic. For cancer therapy, efficacy can, for example, be measured by assessing the time to disease progression (TTP) and/or determining the response rate (RR).

The terms "linked", "joined", "grafted", "tethered", "associated", and "conjugated" in the context of the biocomposite of the invention, are used interchangeably to refer to any method known in the art for functionally connecting moieties (such as biologically active agents), including, without limitation, recombinant fusion, covalent bonding, disulfide bonding, ionic bonding, hydrogen bonding, and electrostatic bonding.

The term "modified" refers to an alteration from an entity's normally occurring state. An entity can be modified by removing discrete chemical units or by adding discrete chemical units.

The term "polypeptides" refers to any polymer comprising any number of amino acids, and is interchangeable with "protein", "gene product", and "peptide".

The term "intercalates" or "interaction" is the immersion or dispersal of one substance into at least a portion of another substance.

The methods of the invention can utilize general techniques known in the field of polymer chemistry. General polymer chemistry concepts and methods that may be utilized are described in the Polymer Handbook (4$^{th}$ Edition), eds., Brandup et al., New York, John Wiley and Sons, 1999; and Polymer Synthesis and Characterization: A Laboratory Manual, eds. Sandler et al., Academic Press, 1998. The practice of the subject invention can employ, unless otherwise indicated, conventional techniques of molecular biology, microbiology, recombinant DNA technology, electrophysiology, and pharmacology, which are within the ordinary skill in the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover ed. 1985); Perbal, B., A Practical Guide to Molecular Cloning (1984); the series, Methods In Enzymology (S. Colowick and N. Kaplan eds., Academic Press, Inc.); Transcription and Translation (Hames et al. eds. 1984); Gene Transfer Vectors For Mammalian Cells (J. H. Miller et al. eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. eds. (1991) IRL Press)).

Following are examples that illustrate procedures for practicing the invention. These examples should not be construed as limiting. All percentages are by weight and all solvent mixture proportions are by volume unless otherwise noted.

Example 1

Production of Synthetic Elastic Polymer/Collagen Fibril Biocomposite

Radical emulsion polymerization was employed to synthesize an ethyl acrylate-methyl methacrylate copolymer emulsion, which, when in solid film form, displays mechanical properties comparable to elastin. Briefly, the liquid emulsion was then mixed in various ratios with native sea cucumber collagen fibrils, from which fibers were formed. Mechanical analysis was then performed on the fibers.

Production of the fibril biocomposites will now be described in more detail. Emulsions are formed through radical emulsion polymerization at 70° C. under a nitrogen environment for 6-8 hours. Add 25-150 mL of concentrated (20% solid content) ethyl acrylate-methyl methacrylate (4:1) emulsion (KRG3) to 10 mL of sea cucumber collagen fibrils in water and place mixture in dialysis tubing. Gently mix the solution for even distribution of polymer, then place the tubing in 3% acetic acid overnight for fiber formation. The fibers are then removed from the tubing and allowed to air dry by slowly lifting them from the acetic acid solution. The dry fibers were cut into pieces of approximately 15 mm in length for mechanical analysis.

Example 2

Characterization of Synthetic Elastic Polymer/Collagen Fibril Biocomposite

Figure 1A:
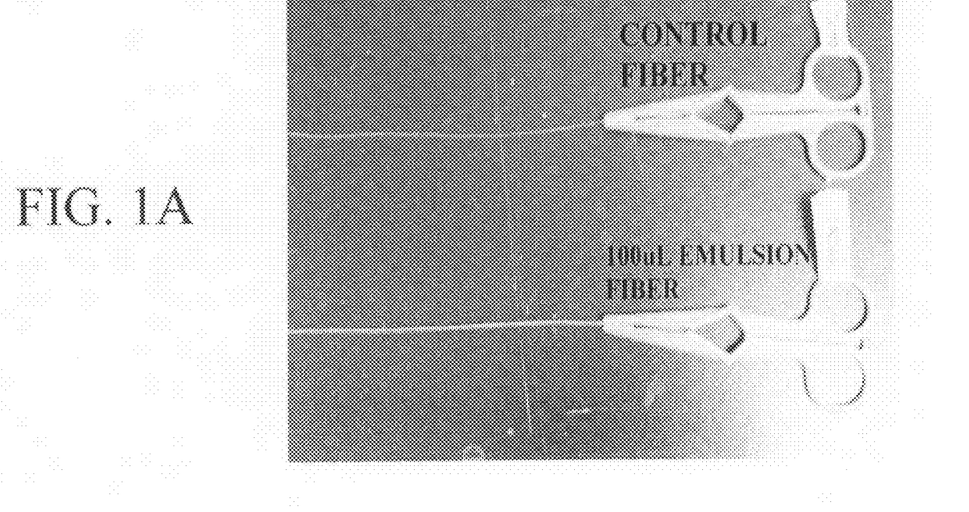
FIGS. 1A and 1B show, adjacent a control collagen fiber, segments (approximately 15 mm in length) of embodiments of fibril biocomposites of the invention, prepared by radical emulsion polymerization to synthesize a liquid ethyl acrylate-methyl methacrylate copolymer emulsion, which was then mixed in various ratios with native sea cucumber collagen fibrils, from which the fibril biocomposites were formed.
Figure 1B:
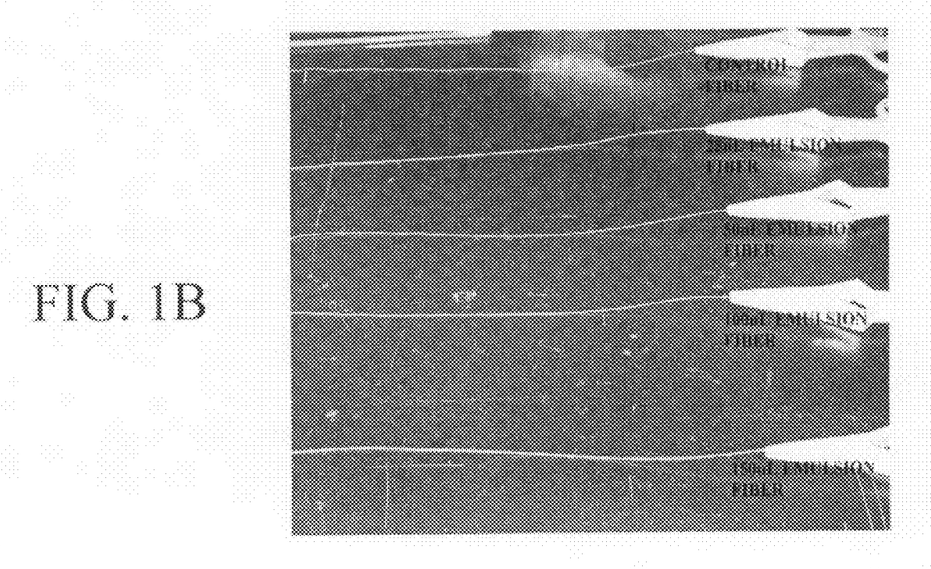
Figure 2A:
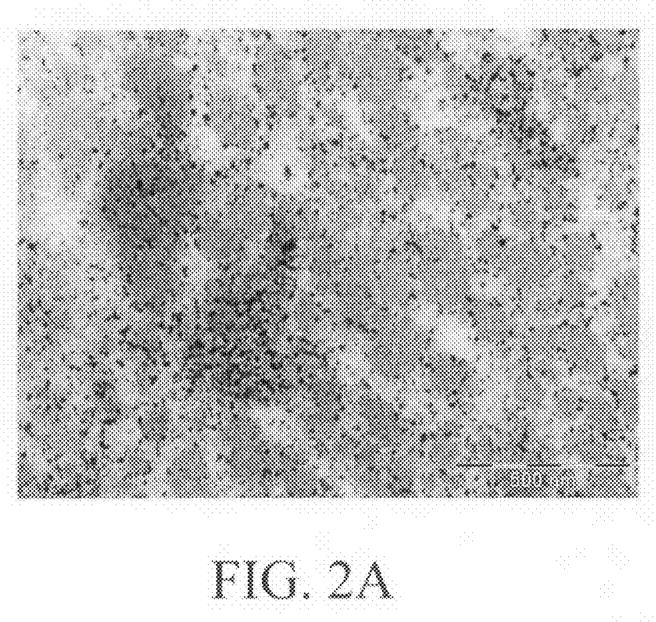
Figure 2B:
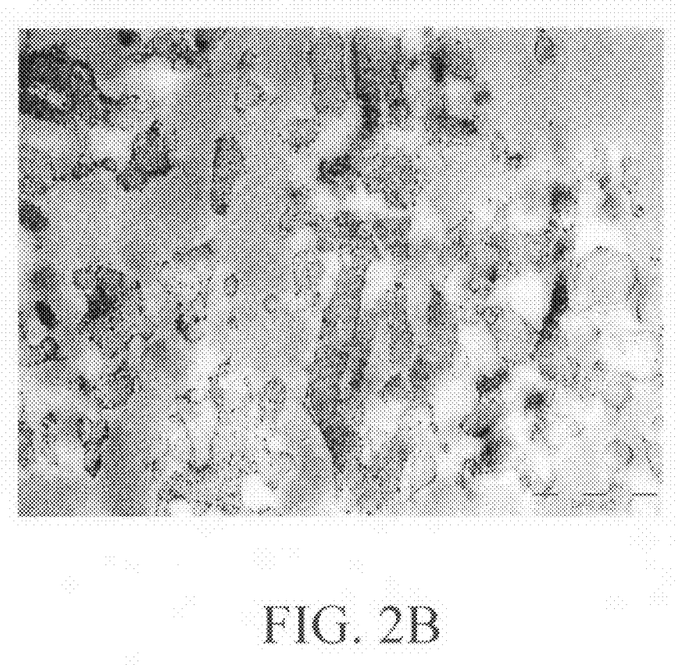

FIGS. 2A and 2B are TEM of a cross-section of a control collagen fiber (FIG. 2A) and KRG3-treated fiber (FIG. 2B). The control fiber contains mainly linearly-arranged fibrils tightly packed in the fiber in a longitudinal orientation. The emulsion-treated fibrils do not appear to have a linear arrangement and are also much more loosely arranged within the fiber. The spatial difference in the composite fiber is due to the intertwining of the emulsion with the fibrils during fiber formation. The random orientation is most likely a factor of the mixing performed when the emulsion is introduced.

Figure 3A:
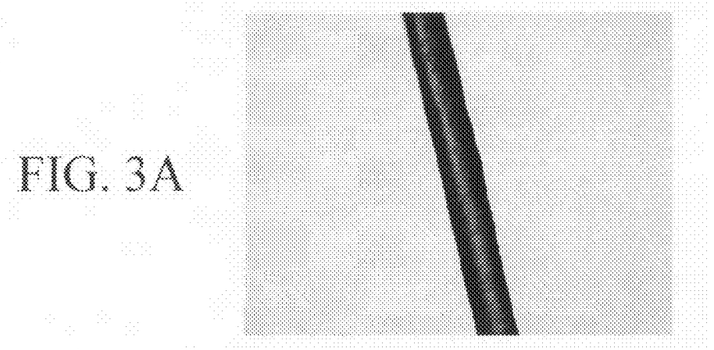
FIGS. 3A-3D show micrographs of dry and wet collagen fibers and dry and wet biocomposite fibers of the invention. Dry control collagen fibers (FIG. 3C) are twice as strong as the dry biocomposite fibers (FIG. 3A), but when hydrated (as would the material would be in biological applications), the wet biocomposite fibers (FIG. 3B) are up to 40 times stronger than the wet collagen fibers (FIG. 3D). The mechanical properties of the collagen fibers change drastically when hydrated, and a large degree of swelling is observed (FIG. 3C to 3D), but there is little to no differences observed for the mechanical properties of the biocomposite materials, and very little swelling was observed for these fibers (FIG. 3A to 3B). Thus, the biocomposite is able to retain its mechanical properties in a moist environment.
Figure 3B:
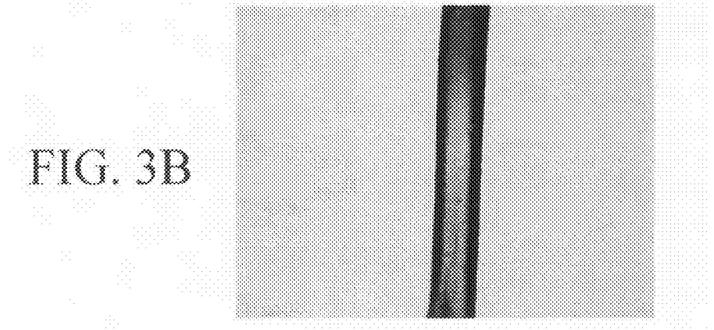
Figure 3C:
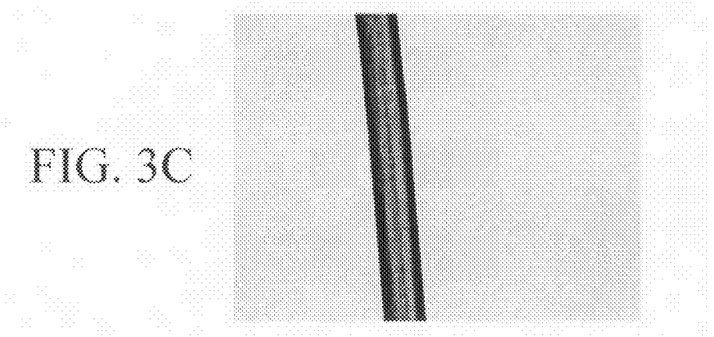
Figure 3D:
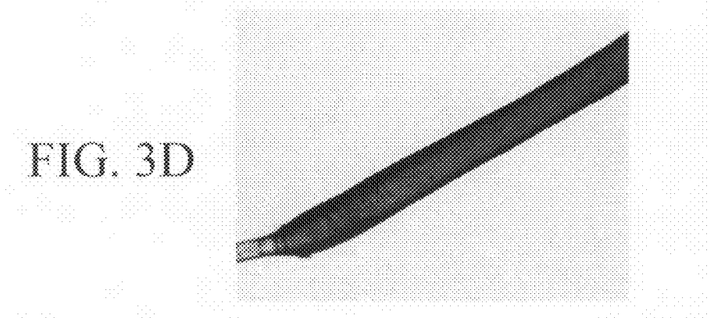
Figure 4:
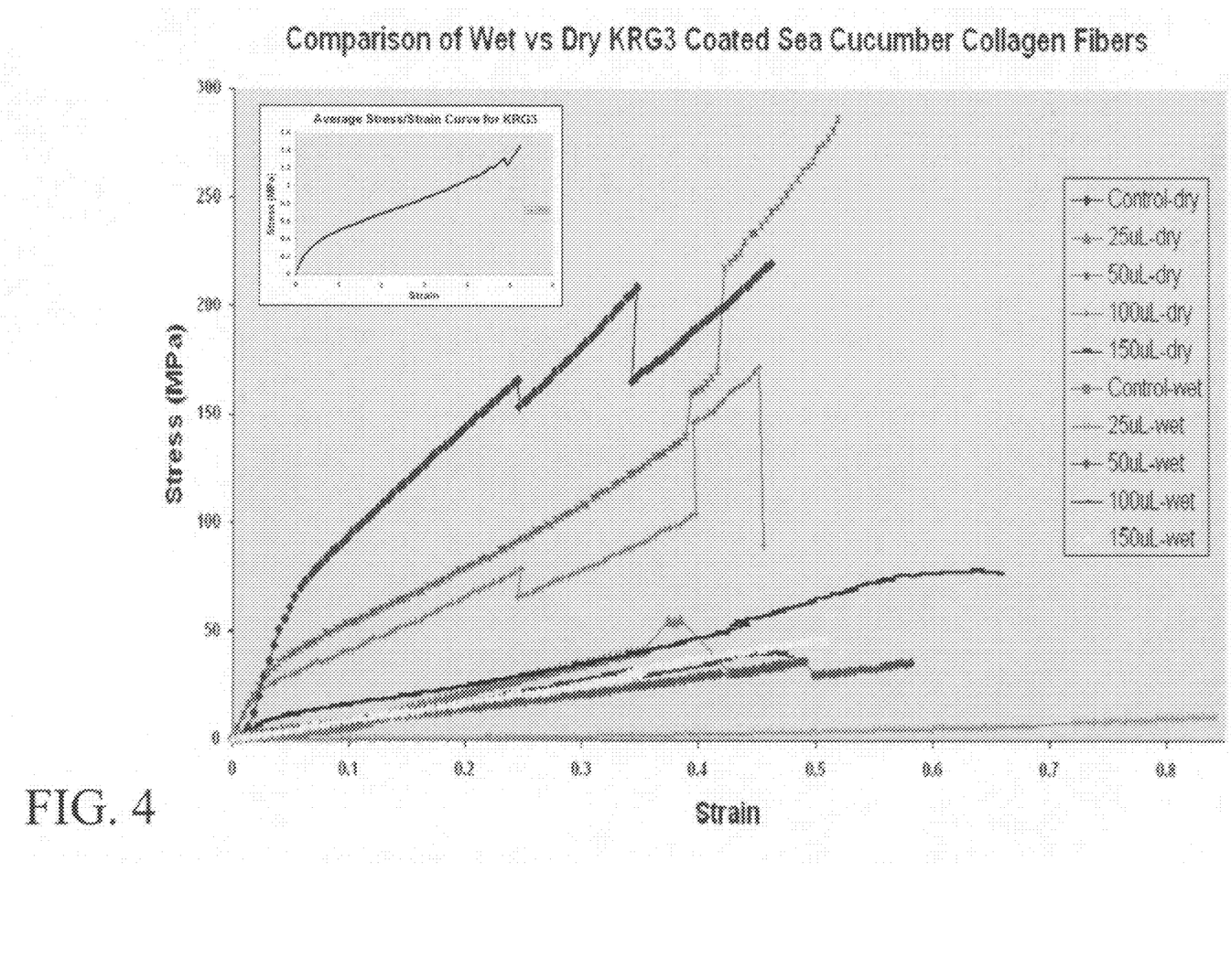
FIG. 4 is a graph comparing stress and strain in wet versus dry KRG3 coated sea cucumber collagen fibers.

Dry control collagen fibers (FIG. 3C) are twice as strong as the dry biocomposite fibers (FIG. 3A), but when hydrated (as would the material would be in biological applications), the wet biocomposite fibers (FIG. 3B) are up to 40 times stronger than the wet collagen fibers (FIG. 3D). The mechanical properties of the collagen fibers change drastically when hydrated, and a large degree of swelling is observed (FIG. 3C to 3D), but there is little to no differences observed for the mechanical properties of the biocomposite materials, and very little swelling was observed for these fibers (FIG. 3A to 3B). Thus, the biocomposite is able to retain its mechanical properties in a moist environment.

Figure 5A:
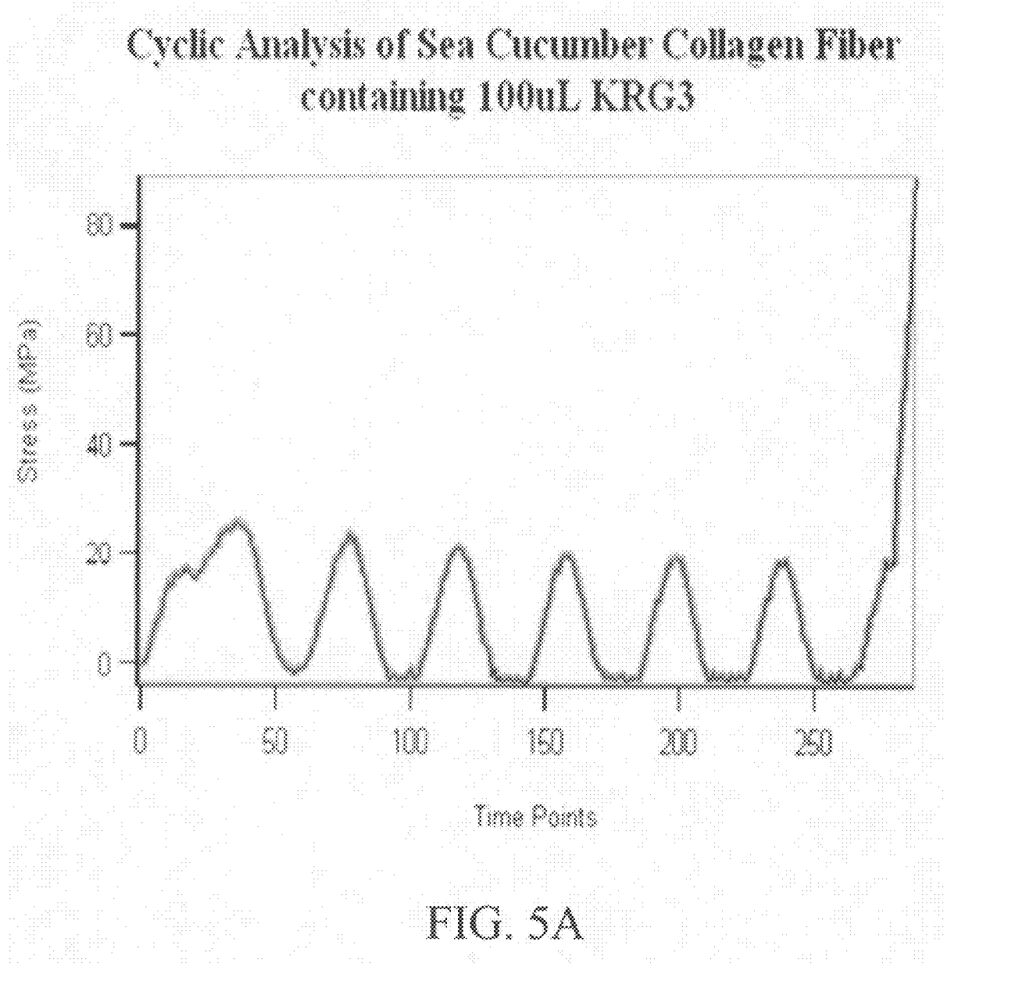
FIGS. 5A and 5B are graphs showing cyclic analysis of sea cucumber collagen fiber containing 100 μL KRG3 (FIG. 5A) and mechanical analysis of calcium treated kRG3 polymer/collagen biocomposite fibers (FIG. 5B).

The maximum tensile strength after a 25-cycle analysis is in the same range as the fiber un-fatigued; therefore, cyclic analysis did not alter the overall strength of the fiber. There is a slight decrease in strength between each cycle, but the overall max strength remains constant. Little deformation was observed on the fiber by the repeated cyclic displacement.

Figure 5B:
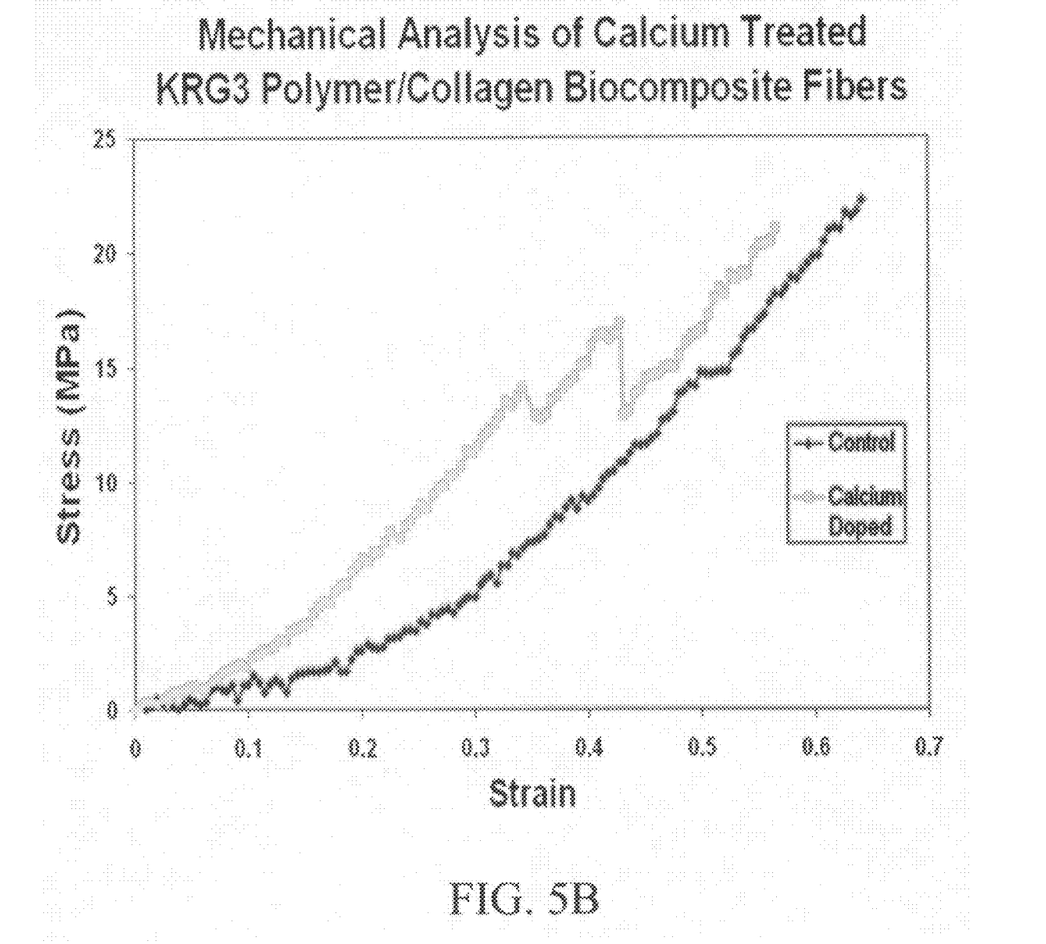

Both fibers appear to display relatively the same mechanical properties. While the calcium-doped fibers appeared to be slightly stiffer (less strain observed), the maximum tensile strength for each set of fibers was equivalent, thus the calcium treatment had no effect on the fiber's tensile strength.

TABLE 1

|  | Control | 25 uL | 50 uL | 100 uL | 150 uL |
|---|---|---|---|---|---|
| Wet Fibers | | | | | |
| Force (N) | 0.131144 | 2.295319 | 4.5605 | 4.230542 | 3.516884 |
| Stress (MPa) | 1.154574 | 7.458517 | 36.03989 | 41.75548 | 32.92559 |
| Strain | 0.187441 | 0.707732 | 0.490528 | 0.42103 | 0.370264 |
| Young's Modulus (MPa) | −9.47825 | 3.224868 | 67.08264 | 89.95072 | 87.40711 |
| % Swell | 102.9298 | 36.85137 | 56.77656 | 33.57825 | 23.21725 |
| Dry Fibers | | | | | |
| Force (N) | 5.36957 | 3.052235 | 5.047687 | 3.774777 | 4.890496 |
| Stress (MPa) | 222.9718 | 44.16573 | 172.4999 | 114.4796 | 59.32537 |
| Strain | 0.356441 | 0.378474 | 0.439481 | 0.372034 | 0.496644 |
| Young's Modulus (MPa) | 614.0175 | 120.3238 | 279.1168 | 224.6649 | 96.0726 |

The composite fibers displayed the most advantageous property of each individual constituent: they preserve the high tensile strength of collagen while sustaining the long range elasticity of the polymer films. The degree of fiber stiffness and elasticity is easily controlled by varying the ratios of polymer to collagen. The ability to retard swelling of the fibers was also achieved in the composite fibers. Biocompatibility of the polymer has been established in vitro against human dermal fibroblasts; therefore, the formation of polymer/collagen composite fibers is an important step toward implementation of biocompatible materials for artificial tissue.

All patents, patent applications, provisional applications, and publications referred to or cited herein, supra or infra, are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method for producing a synthetic biocomposite comprising a biotic material and an abiotic material, wherein the biotic material is collagen and the abiotic material is a polymer produced by polymerizing, monomers, wherein said method comprises polymerizing the monomers by emulsion polymerization to form an emulsion, and mixing the biotic material with the emulsion, followed by drying, thereby forming the synthetic biocomposite.

2. The method of claim 1, wherein the biotic material is collagen fibrils and the biocomposite is formed as a fiber.

3. The method of claim 1, wherein the abiotic material comprises a copolymer.

4. The method of claim 3, wherein the copolymer is ethyl acrylate-methyl methacrylate.

5. The method of claim 1, wherein the biocomposite further comprises a biologically active agent.

6. The method of claim 5, wherein the biologically active agent is a cell.

7. The method of claim 1, wherein polymerization is conducted under nitrogen.

8. The method of claim 1, wherein polymerization comprises emulsifying the monomer in water and a surfactant and polymerizing using a radical initiator.

9. The method of claim 8, wherein the polymerization is conducted under nitrogen at about 70° C. for about 6 to 8 hours.

10. The method of claim 8, wherein the radical initiator is a peroxide, persulphate, alkyl hydroperoxide, thiosulphate, metabisulphite, or hydrosulphide.

11. The method of claim 1, wherein the monomer is acrylonitrile, acrylic acid, maleic acid, methyl acrylate, ethyl acrylate, butyl acrylate, butyl methacrylate, 2-ethylhexyl acrylate, methoxyethyl acrylate, dimethylamino acrylate, methacrylic acid, isobutyl methacrylate, 2-ethyl hexyl methacrylate, lauryl methacrylate, stearic methacrylate, dimethyl amino methacrylate, allyl methacrylate, 2-hydroxyethyl acrylate, 2-hydroxy propyl acrylate, 2-hydroxy ethyl methacrylate, modified acrylamide, modified methacrylamide glycidyl acrylate, styrene, vinyl acetate, vinyl toluene, or a synthetically modified acrylic.

\* \* \* \* \*

UNITED STATES PATENT AND TRADEMARK OFFICE
CERTIFICATE OF CORRECTION

| | | |
|---|---|---|
| PATENT NO. | : 8,093,027 B2 | Page 1 of 1 |
| APPLICATION NO. | : 11/901209 | |
| DATED | : January 10, 2012 | |
| INVENTOR(S) | : Edward Turos, Thomas J. Koob and Kerriann Robyn Greenhalgh | |

It is certified that error appears in the above-identified patent and that said Letters Patent is hereby corrected as shown below:

Column 14
Lines 41-42, "phenyloin" should read --phenytoin--.

Signed and Sealed this
Fifteenth Day of May, 2012

David J. Kappos
*Director of the United States Patent and Trademark Office*